United States Patent
Miller

(10) Patent No.: US 7,326,172 B2
(45) Date of Patent: Feb. 5, 2008

(54) ACTIVE TISSUE AUGMENTATION MATERIALS AND METHOD

(75) Inventor: Paul Leonard Miller, Harvest, AL (US)

(73) Assignee: Torax Medical, Inc., Maple Grove, MN (US)

( * ) Notice: Subject to any disclaimer, the term of this patent is extended or adjusted under 35 U.S.C. 154(b) by 315 days.

(21) Appl. No.: 10/804,604

(22) Filed: Mar. 18, 2004

(65) Prior Publication Data
US 2006/0009674 A1    Jan. 12, 2006

Related U.S. Application Data

(63) Continuation of application No. 10/371,012, filed on Feb. 20, 2003, now abandoned, which is a continuation of application No. 09/634,414, filed on Aug. 8, 2000, now abandoned.

(51) Int. Cl.
A61F 2/00    (2006.01)

(52) U.S. Cl. ........................................... 600/29

(58) Field of Classification Search ........... 600/29–32; 128/897–899, DIG. 25; 604/96.01
See application file for complete search history.

(56) References Cited

U.S. PATENT DOCUMENTS

| | | | |
|---|---|---|---|
| 3,642,004 A | 2/1972 | Osthagen et al. | |
| 3,750,194 A | 8/1973 | Summers | |
| 3,812,841 A | 5/1974 | Isaacson | |
| 3,926,175 A | 12/1975 | Allen et al. | |
| 3,939,821 A | 2/1976 | Roth | |
| 3,952,726 A | 4/1976 | Hennig et al. | |
| 3,991,743 A | 11/1976 | Bucalo | |
| 4,024,855 A | 5/1977 | Bocalo | |
| 4,053,952 A | 10/1977 | Goldstein | |
| 4,154,226 A | 5/1979 | Hennig et al. | |
| 4,209,010 A | 6/1980 | Ward et al. | |
| 4,258,705 A | 3/1981 | Sorensen et al. | |
| 4,595,390 A | 6/1986 | Hakim et al. | |
| 4,652,257 A | 3/1987 | Chang | |
| 4,773,393 A | 9/1988 | Haber et al. | |

(Continued)

FOREIGN PATENT DOCUMENTS

DE    27 17 607    10/1978

(Continued)

OTHER PUBLICATIONS

Scott et al., "Treatment of urinary incontinence by implantable prosthetic sphincter," Urology, vol. 1, pp. 252-259, (1973).

(Continued)

*Primary Examiner*—John P. Lacyk
(74) *Attorney, Agent, or Firm*—Ropes & Gray LLP; Robert R. Jackson

(57) ABSTRACT

Active tissue augmenting agents, compositions and methods for use are disclosed. In a typical embodiment, the active augmenting agents of the invention can be used to form an artificial sphincter around a lumen of a human or animal body. In one embodiment, the active augmenting agent comprises magnitizable particles which can provide occlusion of a lumen, such as the urethral lumen, by circumferential attraction of the injected material toward the center of the lumen by the inherent magnetic flux field created from the magnetic dipoles of the magnetic particles.

34 Claims, 1 Drawing Sheet

U.S. PATENT DOCUMENTS

| | | | |
|---|---|---|---|
| 4,786,276 A | 11/1988 | Haber | |
| 4,803,075 A | 2/1989 | Wallace et al. | |
| 4,832,680 A | 5/1989 | Haber et al. | |
| 4,865,588 A | 9/1989 | Flinchbaugh | |
| 4,969,474 A | 11/1990 | Schwarz | |
| 4,994,019 A | 2/1991 | Fernandez et al. | |
| 5,004,454 A | 4/1991 | Beyar et al. | |
| 5,007,940 A | 4/1991 | Berg | |
| 5,041,092 A | 8/1991 | Barwick | |
| 5,099,013 A | 3/1992 | Balazs et al. | |
| 5,140,999 A | 8/1992 | Ardito | |
| 5,176,618 A | 1/1993 | Freedman | |
| 5,236,410 A | 8/1993 | Granov et al. | |
| 5,336,263 A | 8/1994 | Ersek et al. | |
| 5,366,506 A | 11/1994 | Davis | |
| 5,451,406 A | 9/1995 | Lawin et al. | |
| 5,509,888 A | 4/1996 | Miller | |
| 5,562,598 A | 10/1996 | Whalen et al. | |
| 5,655,546 A | 8/1997 | Halpen | |
| 5,713,877 A | 2/1998 | Davis | |
| 5,755,658 A | 5/1998 | Wallace et al. | |
| 5,762,599 A | 6/1998 | Sohn | |
| 5,921,244 A * | 7/1999 | Chen et al. | 128/897 |
| 5,997,467 A | 12/1999 | Connolly | |
| 6,074,341 A | 6/2000 | Anderson et al. | |
| 6,251,064 B1 | 6/2001 | Silverman et al. | |
| 6,296,607 B1 | 10/2001 | Milbocker | |

FOREIGN PATENT DOCUMENTS

| | | |
|---|---|---|
| DE | 30 11 742 | 10/1981 |
| DE | 31 39 811 | 4/1983 |
| WO | WO 93/19702 | 10/1993 |
| WO | WO 98/44965 | 10/1998 |
| WO | WO 00/54835 | 9/2000 |
| WO | WO 01/47431 | 7/2001 |

OTHER PUBLICATIONS

Kaufman, B., "Treatment of post-prostatectomy urinary incontinence using a gel prostheses," Urology, vol. 45, pp. 646-653, (1973).

Alksne, J. et al., "Iron-acrylic compound for sterotaxic aneurysm thrombosis," J. Neurosurg., vol. 47, pp. 137-141 (Aug. 1977).

Malizia et al., "JAMA," vol. 251, No. 24, pp. 3277-3281 (1984).

Gruneberger, A.D., "Entwicklung eines magnetischen Urethralverschlusses und erste klinische Erfahrungen," Urologe A, vol. 26, pp. 106-111 (1987) (English summary).

Gruneberger, A.D., "Klinische Erfahrungen mit einem magnetischen Harnrohrenverschluß," Geburtsch. U. Frauenheilk, vol. 50, pp. 150-154 (1990) (English summary).

Gruneberger, A.D., "Modifikation der Anwendung der Magnetschale des Harnrohrenverschlusses bei Rezidiv-Inkontinenz," Geburtsch. U. Frauenheilk, vol. 51, pp. 850-852 (1991) (English summary).

Gruneberger, A.D., "Entwicklung eines magnetischen Urethralverschlusses—eine tier-experimentelle Studie," Zentralbl Gynakol, vol. 115, pp. 328-331 (1993) (English summary).

* cited by examiner

ACTIVE TISSUE AUGMENTATION MATERIALS AND METHOD

Cross-Reference to Related Applications

This application is a continuation of U.S. patent application Ser. No. 10/371,012, filed Feb. 20, 2003 now abandoned, which is a continuation of U.S. patent application Ser. No. 09/634,414, filed Aug. 8, 2000 now abandoned, both of which applications are incorporated herein by reference in their entireties.

FIELD OF THE INVENTION

The present invention relates to soft tissue augmentation. In particular the invention provides materials and methods for active augmentation of soft tissue structures. The invention can be particularly advantageous for the treatment of sphincter disorders including urological disorders such as incontinence, vesicoureteral reflux; and gastro-intestinal disorders including gastric fluid reflux, anal sphincter incontinence, etc

BACKGROUND OF THE INVENTION

Urinary incontinence is a dysfunction of the bladder's ability to securely retain urine until an individual intends to void. Causes for urinary incontinence are many and affect all age groups, but tends to be more prevalent in females and the elderly. The major forms of incontinence are stress incontinence, psychogenic incontinence, and trauma, typically surgical trauma to the vesicle neck. The market for amelioration of urinary incontinence is currently estimated at about 4% of the population and growing due to population shifts toward longer lifespans. At the present time, the costs related to urinary incontinence are estimated at between $1.8 and $10 billion in direct and indirect costs.

Current methods for treating urinary incontinence are pharmacological, surgical, behavioral, and prosthetic implant devices. The least intrusive treatment that can achieve desired results is always recommended. However, each of the existing treatments have limitations and drawbacks.

Several surgical procedures and devices for controlling urinary incontinence have been developed and tried with varying degrees of success. Examples of these include bladder suspension procedures, injection of collagen or passively inert constrictive materials procedures, and various combinations of these.

Behavioral treatment is useful in cases of minor dysfunction, while exercises can help minimize the effects in stress incontinence. Injectable implants of collagen have proven to be successful in mild cases, but are of limited long term use as the collagen is absorbed by the body over a relatively short period of time and must constantly be replaced.

The use of a long term prosthetic device has, historically, been the least desirable as these devices can cause irritation to the of the urethra and ultimately tissue necrosis if the prosthetic device causes circulatory insufficiency. In addition, the application of the obturating collars of some older devices required that the urethra be severed and reattached, further complicating the surgical procedure and causing additional trauma to the tissue.

Prosthetic devices based on the compression of the urethra at a given point are known and disclosed in, for example, "Treatment of urinary incontinence by implantable prosthetic sphincter," by Bradley and Timm, Urology, 1:252 (1973); "Treatment of post-prostatectomy urinary incontinence using a gel prostheses", by Kaufman, Brit. J. Urol., 45:646 (1973) and "Treatment of post-prostatectomy urinary incontinence using a silicon gel prostheses", Brit, J Urol, 48:646 (1973).

In the practice of plastic and reconstructive surgery, inert materials have frequently been implanted to fill in defects or augment weakened tissue. These have been fabricated from a variety of materials and have been implanted using several techniques. Certain very small particle species compounded in a lubricious material have been implanted by subcutaneous injection for both soft and hard tissue augmentation. However, undesirable subsequent particle migration and granulomatous reactions have commonly resulted. This is well documented with such materials as polytetrafluoroethylene (PTFE) particles of very small diameter (>90% with a diameter <30 microns) in glycerin. One such product includes PTFE particles suspended in glycerin with a minor amount of polysorbate and is available under the name Polytef® (Mentor Corp. of California). This is discussed, for example, in Malizia, et al., JAMA, Volume 251, No, 24, pp. 3277-3281 (1984).

U.S. Pat. No. 4,773,393 (the '393 patent) relates to an apparatus for hypodermically implanting a genitourinary prosthesis comprising an extensible, inflatable tissue expanding containment membrane to be located in the proximal periurethral tissues to add bulk to these tissues and thereby overcome urinary incontinence by means of localized, controlled tissue volume increase. In column 1, reference is made to the aforementioned JAMA article co-authored by a co-patentee of the '393 patent, Anthony A. Malizia, with respect to the widespread migration of Polytef® particles along with granulomas. The invention of the '393 patent is said to obviate these problems by providing a prosthesis comprising an elastomerical biocompatible containment membrane into which a biomeric fluid or suspended particulate matter such as TEFLON particles is percutaneously injected to inflate the membrane.

The use of very small diameter particulate spheres (approximately 1-2.0 microns) or small diameter elongated fibrils, (generally 1-20 microns in diameter) of various materials such as cross-linked collagen or synthetic polymers suspended in an aqueous medium to which a biocompatible fluid lubricant has been added as an injectible implant composition is disclosed in U.S. Pat. No. 4,803,075. While these materials create immediate augmentation, the result is generally short-lived as the material also has a tendency to migrate and/or be reabsorbed from the injection site by the host tissue.

Recently, three companies have indicated in published reports their intent to enter the market for treatment of urinary incontinence with an injectible material. Mentor Corporation has received limited approval from the FDA for use of their injectible material, "Urethrin", in treating incontinent male post-prostatectomy patients. Previous published reports stated that C. R. Bard, Inc, and Collagen Corporation were developing an incontinence treatment called "Contigen Bard Collagen Implant," understood to be Collagen Corporation's "Contigen" injectible bovine collagen material. Subsequently, it was reported that: C. R. Bard is also evaluating for urinary incontinence treatment a product called "Hylagel-Muscle" which is said to be based upon technology disclosed in U.S. Pat. No. 5,099,013 directed to modifying naturally occurring hyaluronan "to form three-dimensional sponge-like matrixes in the form of high molecular mass fluids, gels and solids that can separate tissue, cells, and molecules."

Artificial sphincters have been advanced in the prior art and the primary ones in use utilize an inflatable cuff surrounding a conduit to obturate material flow. In creating the localized pressure necessary to overcome the material back pressures, the cuff type devices also tend to obstruct the normal flow of blood in the conduit walls, and thus long term usage of cuff-type artificial sphincters is not viable. The continuous ring of pressure without adequate blood flow can result in scarring and localized tissue damage.

A type of a magnetically actuated artificial sphincter is disclosed in U.S. Pat. No. 3,926,175 showing a cuff having a section that is actuated by magnetic force to press against a conduit around which the cuff is placed. An external electromagnet is utilized for providing the force, and thus the device is not totally implantable, and is made so it will snap to a locked position and must be snapped back to an open position. While the device is made to apply forces only on two opposite sides of the conduit that it is surrounding, rather than in a noose-like complete ring, in order to prevent necrosis, the unit is still difficult to operate, and varying the closing pressure is difficult because the magnet used is for actuation of an over center actuating device.

U.S. Pat. No. 4,024,855 discloses a magnetic filament which may be implanted in the form of a pair of coils on opposite sides of a body tube such as a urethra. Both coils can be permanent magnet materials, or one can be a permanent magnet and the other a filament that has magnetic properties. The coils that are implanted are polarized so that they attract each other for the purposes of pinching the conduit or urethra closed. Then, in order to open the body conduit it is necessary to provide an external unit that creates a magnetic field which alters the polarity of the implanted coils so that the coils repel each other to open the tube. When drainage is over, the external power unit is used to return the implanted coils to their original polarity. It can be seen that such devices have limitations in the force that can be generated, and require the use of external controls for operation. Further, as a practical matter, controlling the pressure on the body conduit using these devices is so that leakage or dripping do not occur. Also, the coils can cause closure which is too tight and thus, can cause damage to the tissue as well.

A magnetically actuated device for controlling a tube that carries fluid flow to or from different organs of the body of a human is disclosed in U.S. Pat. No. 4,053,952 (the '952 patent). This device uses a type of valve arrangement which has a coil with oppositely facing contact members on opposite sides of the tube. When current is supplied to demagnetize, or magnetize permanent magnets installed, the tube can selectively be blocked or opened. An external current of substantial value is required in order to operate the unit, and while it is indicated that power consumption is low, there still is a need for external power. The device shown in the '952 patent can be used as a pump as well by alternately magnetizing and demagnetizing the permanent magnets.

U.S. Pat. No. 4,994,019 discloses the use of an active magnet mechanism and appliance for the control of incontinence that must be controlled by external stimuli and must be surgically inserted through significantly invasive surgery. Finally, U.S. Pat. No. 5,509,888 teaches the use of magnetorheological fluids housed in a chamber and which react within an applied magnetic flux to radically change their viscosity and other rheological properties to form an artificial sphincter.

Magnetically controlled plugs have also been advanced for controlling incontinence, and such devices are shown in German Patent Nos. DE2717607 and DE3139811.

From the foregoing discussion, it will be appreciated that many approaches and treatments have been proposed to cure or relieve conditions of urinary incontinence. While some of these approaches have enjoyed modest success, relief has been for the most part, only temporary in those patients where success is noted. Thus, there remains a continuing need for improving treatment of such urological disorders.

SUMMARY OF THE INVENTION

The invention is directed to actively augmenting tissues in human and animal bodies. The disclosure provides active augmenting agents and methods particularly advantageous for forming artificial sphinters to selectively occlude lumens throughout the body.

It will be noted that in several places throughout the specification, guidance is provided through lists of examples. In each instance, the recited list serves only as a representative group. It is not meant, however, that the list is exclusive.

In one embodiment an active augmenting agent includes magnetizable particles. The magnetizable particles can be magnetized prior to depositing into a tissue or unmagnetized particles can be deposited into the tissue and subsequently magnetized after deposition into tissue. According to this embodiment, the magnetically active particles can have a nominal measurement of between about 30 and 3000 microns (0.003 to 3.0 mm). A preferred range for many applications is between about 80 and 600 microns (0.008 to 0.6 mm). The magnetically active particles can have generally amorphous surfaces and typically possess surface irregularities including indentations.

Magnetizable particles according to the invention can be suspended in a suitable biocompatible carrier. Examples of suitable bicompatible carriers include saline, solutions of sodium hyaluronate, various starches, hydrogels, polyvinylpyrrolidones, other polymeric materials, polysaccharides, organic oils or fluids, etc. The patient's own plasma can also be a suitable carrier. The plasma may be derived from blood withdrawn from the patient, centrifuged to remove cells (or not) and mixed with appropriate aliquots of particles and the mixture injected in the desired locations.

A suspension of magnetically active particles according to the invention provides an active device that utilizes magnetic particles in such a way as to prevent absorption by macrophages while providing a compliant surface to the urethra in order to prevent circulatory insufficiency. When deposited in tissue surrounding a lumen, for example the urethral lumen, the small, permanent magnetic fields created by the magnetically active particles can cause an artificial increase in the viscosity and apparent density of the suspension.

Thus, in one embodiment, the invention provides an injectible, magnetically active control media and method providing a unique solution to the growing number of people suffering from urinary incontinence due to sphincter insufficiency. The injectible magnetically active media addresses the shortcomings of many existing products and procedures available to physicians and supplies a unique solution to restoring individual control over bladder function.

Other embodiments of the invention are further described herein below.

DETAILED DESCRIPTION

Figure 1:
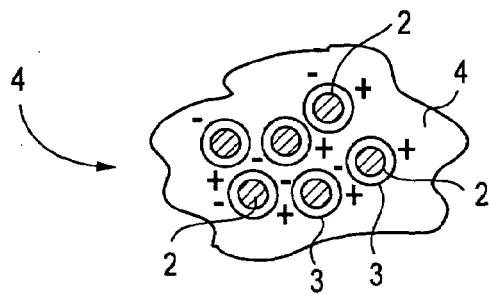
FIG. 1 illustrates an exemplary embodiment of an augmenting composition according to the invention.

The present invention is directed to active tissue augmenting agents, compositions and procedures for active tissue augmentation when the agents are deposited at selected locations within or near a tissue to be augmented. In some embodiments, passive tissue augmentation can also occur due to the bulk of the compositions deposited within the tissue. The invention is particularly advantageous for amelioration of sphincter disorders in humans and animals.

As used herein, to "augment" a tissue means to cause the tissue to have an increase in size or a change in configuration relative to the size or configuration of the tissue prior to augmentation. "Active augmentation" means that the tissue configuration is altered as a result of an attracting or repelling force exerted by an agent deposited in or near the tissue. In contrast, "passive augmentation" means that the tissue configuration is altered as a result of volumetric displacement of the tissue contours due to the volume of a substance deposited in or near the tissue. As used herein, unless otherwise specified, "tissue" typically refers to soft tissue (i.e., non-bone structures) throughout the body including, for example, fat, muscle, collagen, mucosa, submucosa, vasculature, etc.

According to the invention, an "active augmenting agent" is a substance which when deposited within a tissue at a first location can be drawn towards a second location of tissue containing the same or a different substance due to an attraction between the substance at the first and second locations. In some preferred embodiments, an active augmenting agent includes compounds susceptible to a magnetic dipole. Examples of active augmenting agents susceptible to a magnetic dipole include magnetizeable particles such as iron, steel, cobalt, nickel, samarium, etc. or alloy particles that are or can be treated to be attracted to iron and produce a magnetic field external to themselves. As used herein, the term "particles" includes material configurations such as beads, spheroids, cubes, rods, shavings, trapezoids, rectangles, etc. An active augmenting agent of the invention may also provide passive augmentation of a tissue as a result of the volume of the agent, or composition including the agent, that is injected into the tissue.

In a typical embodiment, an active augmenting agent can be administered in or near a tissue to be actively augmented. The agents are preferably fluids, solids or combination of fluids and solids which are flowable and can be deposited into tissue through minimally invasive techniques such as through a hypodermic needle or similar delivery device that provides for positioning an outlet for release of the agent at a selected deposit site. In an alternative embodiment, it is foreseen that an augmenting agent in the shape of small rods (e.g., 5 mm length and 1 mm diameter) can be placed in tissue through minimally invasive or non-minimally invasive methods.

Thus, for exemplary purposes, in one embodiment, an active augmenting agent can be deposited in the submucosal tissue surrounding the urethra to treat a patient affected by urinary incontinence. The attractive forces of the agent deposited in the submucosa draws the wall of the urethra together to occlude the urethral lumen thereby forming an artificial sphincter. During urine voiding, the force of the urine stream caused by contraction of the bladder can open the artificial sphincter and after voiding the attractive forces of the augmenting agent causes the urethral lumen to return to its constricted state to maintain urinary continence.

The invention is particularly suitable for male or female patients to form artificial sphincters that supplement or supplant natural sphinters in lumens throughout the body including, for example, bladder, gastro-esophogeal, pyloric, iliocecal, anal, etc. Thus, the invention can be used to ameliorate conditions associated with urinary incontinence, vesicoureteral reflux, gastro-esophageal reflux, gastroduodenal reflux, anal incontinence, bowel resection, etc.

An active augmenting agent can include particles that have a size of about 30 to 3000 microns (0.003 mm to 3.0 mm) and preferably, for most applications, about 80 to 600 microns (0.008 mm to 0.6 mm). The particles can be textured or smooth. Typically, smooth particles used for a particular application will be larger than textured particles used for the same application. As will be discussed further below, a biocompatible coating can be applied over the entire surface of the particles to facilitate acceptance of the particles by the body.

The particles of an active augmenting agent can be in a composition that suspends the particles in a biologically compatible carrier. As used herein, "biologically compatible" means that the carriers provide low or no tissue reaction and are removed or metabolized by the body with low or no cytotoxic effects. Suitable biocompatible carriers include, for example, saline, various starches, hydrogels, polyvinylpyrrolidones (PVP), polysaccharides, fats, organic oils or fluids and polymeric materials which are known and used in the art. Particularly advantageous carriers include esters of hyaluronic acids such as ethyl hyaluronate and polyvinylpyrrolidone (PVP). PVP normally has the general empirical formula $[(CHCH_2)_2N(CH_2)_3CO]_n$ wherein "n" is in the range of about 25-500. One form of PVPs are known and marketed as Plasdone™, available from International Specialties, Inc. Wayne, NJ. A patient's own plasma can also be used as a carrier.

A composition of an active augmenting agent can also include a "surface modifier". As used herein, a "surface modifier" connotes a material combined into the formed particle, applied to the surface of the particle or added to the carrier to alter inter-particle or agent-tissue interaction. The surface modifier may also provide particle identifiability (e.g., increased radiopacity), alter the coefficient of friction (e.g., increase lubriciousness), assist in detoxification of the magnetic particle surfaces, render the surface of the particles more amenable to tissue in-growth, facilitate tissue encapsulation of individual particles, etc. Examples of useful surface modifiers include PVP, collagen, hyaluronates, polytetrafluoroethylene (PTFE), and others.

Surface modifiers and/or other biocompatible substances may be incorporated into the carrier or combined with the surface of the particles prior to addition to the carrier. Surface modifiers such as PVP and PTFE may be mixed into the base material used to form the particles. The surface modifiers can provide surface texture to the particles which may then further be coated with a layer of a hyaluronate or hyaluronic acid to provide improved tissue acceptance. Surface modifiers such as PTFE may be admixed with, for example, a poly di-substituted siloxane particle material prior to curing the particle to impart an average surface modification to the cured particle. A material such as hyaluronic acid may be attached to the particle surface either thorough physical or chemical bonding. Surface modifiers such as PVP, collagen, hyaluronates, polytetrafluoroethylene (PTFE) etc. also can be selected to assist in detoxification of the magnetic particle surface and promote tissue encapsulation, if desired.

A composition of the active augmenting agent can contain additional bioactive substances that can be included in the carrier or attached to the surface of the particles to promote encapsulation. Examples of such bioactive substances include fibronectin, transforming growth factor beta, and various other cytokines, such as interleukin-1.

It is believed that once implanted into tissue, the body typically forms a thin layer of scar tissue around each of the particle implants to provide initial encapsulation. Polyvinylpyrrolidone, hyaluronate or collagen or other biocompatible substances may be chemically or physically combined with the particle substance or its surface to enhance the acceptance of the implant by the host. While in most situations the particles are of random size and configuration, but within the constraints of size indicated, it is generally desirable that the particles be of generally uniform size and configuration for use in a given procedure.

By way of further background, the average diameter of a capillary is approximately 16 microns, or approximately two times the diameter of a red blood cell. Therefore, textured magnetically active particles having a size of at least approximately 30 microns, will not be absorbed into the capillaries and generally remain captive and fixed in place. Smaller particles, including some up to the 30 micron range, have been implicated in causing chronic inflammation and may be ingested by host cells. Thus, to reduce the likelihood of chronic inflammation, it is preferred that particles in the range of between about 30 and 3000 microns be used.

Fibroblasts are the scar-forming cells of human and animal bodies. These cells range in size from between about 20 microns up to about 100 microns. Because of contact guidance and reduced motion, they tend to form an efficient scar tissue or collagen-based coating around an inert foreign body. Furthermore, such scar tissue will conform to the irregularities in the surface of the foreign body, particularly if they are of sufficient size to accommodate tissue ingrowth. Studies have shown that foreign substances can be firmly anchored in a predetermined location in the body. Because of the inherent ability of fibroblasts to form scar tissue in and around irregularities of the surface, such anchoring occurs in many locations, including locations within the blood stream.

Inert foreign particulate matter used for tissue augmentation having a mean diameter less than about 30 microns are generally subject to significant migratory loss from the site of injection, regardless of surface configuration, absent extraordinary protection. The size and irregular nature of the surface of some magnetically active spheres of the invention, however, minimizes their migration tendencies and favors benign assimilation in scar tissue.

In many prior compositions of implantable particles, particle size tends to vary over a range. Within any group of particles there will be a percentage of the group larger and a percentage of the group smaller than a target size. That is, the particle size defines a range of sizes. Furthermore, the normal variation in patient to patient acceptance and reaction to tissue injection of magnetically active particles must be considered. With these factors in mind, the invention considers optimum particle size, particularly with regard to the problems of unwanted migration and formation of granulomatous reactions.

Observations in a variety of clinical situations have indicated that particles less than about 60 microns in diameter can be engulfed by macrophages and transported to regional lymph nodes. Submicron-sized particles may be the most easily transported and may remain intracellular indefinitely. However, larger particles, particles that approach the size of a macrophage, i.e., from about 20 to about 60 microns, may cause the death of a cell when engulfed. This begins a progression in which the dead cell releases intercellular enzymes (e.g., cytokines) that then attract other phagocytes which, again, encounter and engulf the particle with the debris of the first encounter. In this manner, a vicious cycle continues on a larger scale as a chronic inflammatory response. Such a response is typically highly undesirable.

Particles greater than about 60 microns, however, have not been observed within a cell or within lymph nodes, and, certainly, particles greater than 80 microns appear safe from initiating such foreign body reactions. Thus, there is theoretically there is no upper limit to the size of particles suitable for use according to the invention. However, for practical purposes the useful upper limit of the dimensions of active augmenting particles will typically be about 1 to 3 mm since particles of a size greater than this may be perceived as surface irregularities when palpated. Moreover, in contrast to larger particles whose physical presence can cause continuous pressure to treated tissue, the physical presence of smaller particles exert relatively discontinuous or intermittent pressure thus allowing uninterrupted blood flow to all portions of the treated tissues Particles suitable for the present invention can be prepared using known methods. Magnetizeable particles of the sizes contemplated for use in the present invention may be manufactured from any number of techniques, such as vapor condensation, spray freezing, roll forming, forging, or stamping. Those skilled in the art of powdered metallurgy will be able to easily recognize how to produce magnetically active particles of the size desired for this invention. Non-limiting examples of preparation methods for some particles are discussed below.

The spray freezing process is commonly used in the operation of a shot tower for making lead shot or in a spray dryer for making powdered milk. In the shot tower procedure the size of the particles can be regulated by varying the orifice size of the dispersing screen. In the spray freezing example the particle size can be varied by regulating the orifice and/or pressure in a nozzle-type unit or the rotational speed of the dispersing head in a rotary disk unit. Additional information on the manufacture of powdered metals is available from the US Government in the military specifications for powdered aluminum (Mil-Std 512A).

In preferred embodiments, magnetically active particles can be manufactured from permanent magnetic material. These materials are defined as having a wide hysteresis loop characterized as having high resistance to a magnetizing force while also possessing a high magnetic flux density. Materials which intrinsically possess such characteristics are high carbon steel, nickel-bearing materials (e.g. Alnico), rare-earth cobalt alloys (e.g. samarium cobalt), or complex rare-earth/iron mixtures such as neodymium-iron-boron alloys. Magnetically active materials are available in metallic or ceramic forms or in combinations of the two materials. Magnetically active materials are described in the American Society of Metals handbook and are well known to those familiar with magnet fabrication. The magnetically active materials disclosed herein are used for illustration purposes only and should not be construed to be restrictive.

In order to have the magnetically active particles be accepted by the biological tissue, an appropriate biocompatible coating is preferably placed over the entire surface. These biocompatible coatings can be manufactured from any number of known biocompatible materials such as titanium or titanium alloys such as Ti-6Al-4V; cobalt based ferrous alloys; nickel alloys such as nickel-titanium alloys or "Nitinol"; ceramic materials such as high density aluminum oxide; carbon compounds such as pyrolytic carbon, vitreous carbon, or vapor deposited carbon on substrates; plastic materials such as medical grades of polyethylene, polypropylene, perfluorinated polymers, acrylic polymers, polyurethanes, or silicone rubbers; or deposited metals such as gold, platinum, or other noble metal.

If desired, surface modifiers can be incorporated as a coating on the surfaces of the particles. In this manner, certain materials such as hyaluronic acid, for example, may be attached to the magnetically active particle surface either through physical or chemical bonding in known manners after formation of the particles and coating with a biocompatible material. The magnetically active particles can then be mixed with the appropriate vehicle in appropriate ratios, placed in containers, and sterilized within the container.

The patient's overall condition must be evaluated for the optimum quantity and strength of an active augmenting agent, such as a magnetic media, in order to achieve optimum control with minimal inconvenience. An optimal pressure range is to maintain approximately 500-1000 Pascals (50-100 cm/$H_2O$) of internal bladder pressure. Thus, for example, a preferred internal bladder pressure for a sedentary individual would be nearer to the lower pressure range and an active person nearer the upper pressure range.

For urinary incontinence, it is foreseen that an active augmenting agent, such as a suspension of magnetizeable particles, can be injected directly into the tissue surrounding the urethral lumen by a physician in an outpatient setting. Current magnetic material technology exists for the magnet properties of the media to last for the lifetime of the individual. Supplemental injections of the media may be needed if the decrease in natural urinary control increases.

Once an active augmenting agent, such as magnetizeable particles are implanted, when the patient has the urge to void urine, the pressure within the bladder increases the radial dimension of the urethral lumen which reduces the magnetic field strength of the particles surrounding the urethra Reducing the magnetic field strength surrounding the urethra reduces the external pressure occluding the urethral lumen permitting urine to be expelled through normal bladder function. Preferably, a suspension of magnetically active particles permits the patient to void naturally without undesirable bladder distention. The radiopaque nature of most medias of the invention will not impair insertion of a urinary catheter to if needed for drainage of the bladder.

The invention will now be further described with reference to the accompanying drawings exemplifying the use of magnetizeable particles according to the invention for the amelioration of stress incontinence. The illustrations and description are for exemplary purposes to facilitate comprehension of the invention and should not be construed to limit the scope of the invention.

In this embodiment, magnetically active particles ranging in size from about 100-600 microns are mixed with a PVP gel to provide a biocompatible biphasic solution. FIG. 1 illustrates an exemplary augmenting composition 1 containing about 200 micron magnetic particles 2 having magnetic dipoles coated in a protective coating 3 and suspended in a carrier 4, such as PVP. The mixture can be contained in a syringe mounted in a pressure injection gun. One example of such a gun is available from Becton-Dickenson, Franklin Lakes, N.J.

Local, regional, or general anesthesia is administered and the patient positioned in the lithotomy position. A cystoscope equipped with a panendoscopic lens is inserted into the urethra and the urethra examined to confirm suitability of submucosal injection. Once suitability has been confirmed, the patient's bladder is filled to about one-fourth to one-half full with a sterile fluid such as water, normal saline, lactated ringers, etc.

Figure 2:
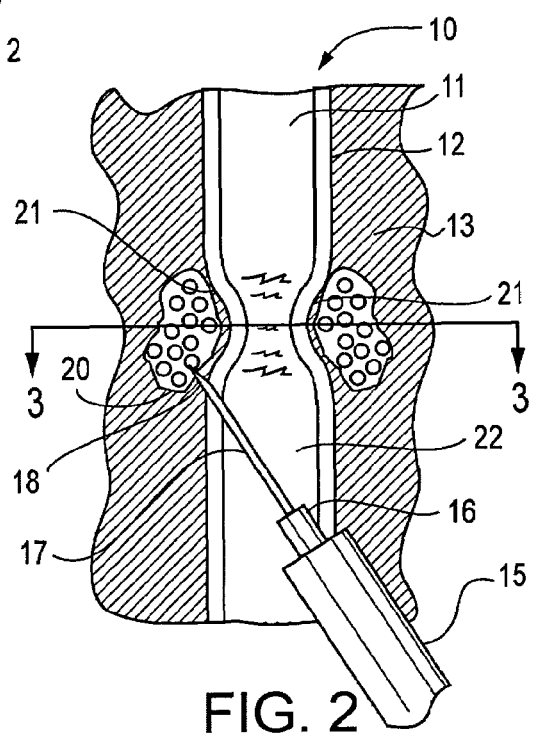
FIG. 2 is a longitudinal cross-sectional view through a urethra according to the invention.

FIG. 2 is a longitudinal cross-section view of a urethra 10 comprising the urethral lumen 11 surrounded by urethral wall 12 and soft tissues 13 external to urethral lumen 11. The augmenting composition 1 can be deposited in the soft tissues 13 by, for example, passing a piercing needle inside the lumen out. That is passing the needle into the urethral lumen 11 and through the urethral wall 12 into the external soft tissue 13.

Alternatively, the composition 1 can be deposited into the external soft tissue 13 through a needle passed into the external soft tissue via the perineum region. The length and gauge of the needle can be selected by the physician. Thus, in one embodiment, a 50 mm 16-gauge needle with a cuff about one centimeter from the distal end can be passed through the working channel of the cystoscope. Alternatively, in another embodiment, a 50 mm 16 gauge needle, without cuff, can be inserted into the soft tissues external to the urethra through the perineum, into the region of the bladder neck. In the former alternative, the needle can be guided by palpation and visual control through the scope. In the latter, the needle can typically be guided by palpation. However, a cystoscope can also be inserted within the urethral lumen when the needle is passed into the external tissue via the perineum to confirm that the needle does not enter the lumen. Other imaging systems known in the art can be used to guide needle placement.

The syringe 15 containing composition 1 is attached to the proximal end 16 of needle 17 and can be mounted in the pressure injection gun (not shown). The distal end 18 of the needle 17 can then be advanced to the six o'clock position 20 and inserted (bevel up) into the submucosal space 21 of tissue 13 approximately 1-3 cm caudal to the bladder neck 22. The position of the distal end 18 of needle 17 can be confirmed by inserting a small amount of the composition 1. If the distal end 18 is properly placed, injection of the agent will form a bump in the submucosa that may be visible in the urethral lumen. It will be appreciated that the radioopacity of some particles can be visualized using known visualization systems, for example x-ray, fluoroscopy, etc.

If the injection site is correct, approximately 1.0 to 5.0 cc will typically be deposited at each injection site. In one embodiment, the injection should elevate the mucosa of the urethral wall 12 into the urethral lumen 11 by a distance of about 2.0 cm. After injecting the composition 1, the needle 17 should remain in place for about 30 seconds. The needle can then be backed away from the injected composition 1 approximately 0.5 cm for 20 seconds after the injection is completed in order to seal the injection site.

Figure 3:
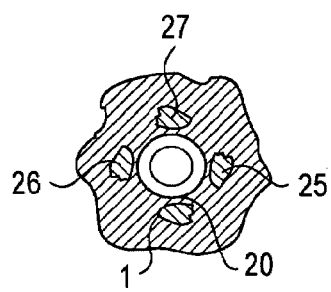
FIG. 3 is a transverse cross-sectional view of the urethra taken through line 3-3 of FIG. 2.

As shown in FIG. 3, which is a cross-section taken through line 3-3 of FIG. 2 of the entire urethra, the injection is then preferably repeated at each of the 3 o'clock 25 and 9 o'clock positions 26 and, if necessary, at the 12 o'clock position 27 or other positions in between.

The magnetizeable particles of an augmenting composition can be injected in the active or magnetized condition. However, in some circumstances, it may be more advantageous to process the magnetizeable particles in a demagnetized state and magnetize them in situ. In such a case, after depositing the magnetizeable particles, a magnetizing wand can be inserted into the urethral lumen and sufficient magnetic flux applied to provide a residual B-field (magnetic flux density) in the injected magnetic particles in situ suitable wands are known and commercially available. The constriction of the urethra can then be measured with the wand and additional magnetic flux applied if necessary. This procedure can also be performed repeatedly at later dates should the patient experience further muscle tone atrophy. In the event of excess radial constriction of the urethra due to overapplication of magnetic flux to the magnetically active particles, the particles can be demagnetized in steps until adequate control is achieved.

Figure 4:
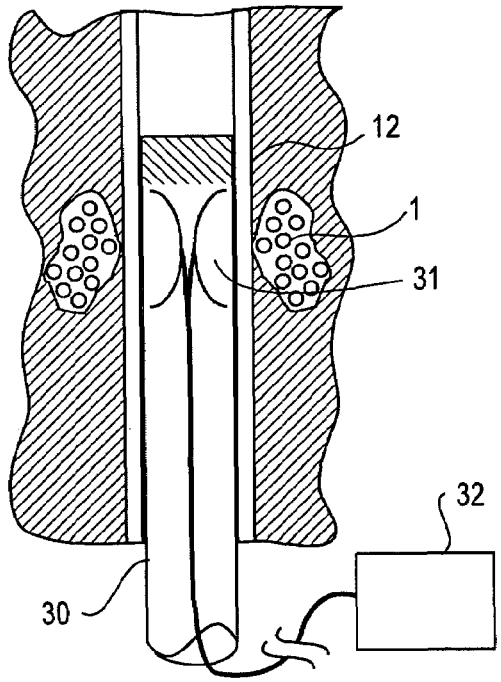
FIG. 4 is a longitudinal cross-sectional view of a urethra with a pressure measuring device passed therein.

FIG. 4 illustrates the use of a measuring device 30 for measuring the pressure of the constricted lumen wall 12 caused by the magnetic flux of injected composition 1. In this illustration, measuring device 30 includes fluid filled membrane 31 connected to a transducer 32.

The increase in the apparent viscosity of the carrier fluid due to the plurality of magnetizeable particles in the composition being attracted to each other causes a controllable radial constriction around the urethral lumen that functionally contributes to the occlusion of the flow of urine while preferably maintaining a constricting force below that of the patient's systolic blood pressure. Because the magnetic flux of the media moves as a packed bed of spheroids, the urethral tissues can continue to be perfused by the circulatory system with reduced likelihood of pressure necrosis caused by the media.

Therefore, in the illustrated embodiment, the invention provides a magnetically active urinary incontinence media deposited in periurethral tissues and can be deposited to form a nearly circular occlusive collar. The magnetically active particles are injected in situ to create a measured circumferential force external to the urethra for the purpose of supplanting, supplementing or augmenting normal sphincter occlusive control. Thus, the invention can provide occlusion of the urethra by circumferential deposition around the urethra of a magnetic agent that causes a radial attraction toward the center of the urethra by the inherent magnetic flux field created from the magnetic dipoles of the magnetic particles. The injectable media can be introduced in the periurethral tissue without the need for invasive surgery for ease of application and minimal tissue insult. Subsequent proximal movement of the media during normal body motion allows for distal re-perfusion of the previously occluded area of the urethra and, therefore, reduces the likelihood of necrosis of the urethral lining and musculature. In addition, both the quantity and magnetic force of the fluid can be adjusted by the attending physician for optimal urine retention and minimal damage to the urethral tissue.

From the foregoing detailed description and examples, it will be evident that modifications and variations can be made in to the instruments and methods of the invention without departing from the spirit or scope of the invention. Therefore, it is intended that all modifications and variations not departing from the spirit of the invention come within the scope of the claims and their equivalents.

What is claimed is:

1. A method of augmenting a soft tissue in a body comprising:
    selecting an active augmenting agent; and
    depositing the active augmenting agent at locations in the soft tissue to be augmented, wherein the active augmenting agent comprises magnetizable particles.

2. The method according to claim 1 wherein the magnetizable particles are suspended in a composition containing biocompatible carrier.

3. The method according to claim 1 wherein the magnetizable particles include a surface modifier.

4. The method according to claim 1 wherein the magnetizable particles are magnetically active prior to depositing into the tissue.

5. The method according to claim 1 wherein the magnetizable particles are unmagnetized when deposited into the tissue and subsequently magnetized after depositing.

6. The method according to claim 1 wherein the magnetizable particles are about 30 to 3000 microns in size.

7. The method according to claim 6 wherein the magnetizable particles are about 80 to 600 microns in size.

8. The method according to claim 1 wherein the active augmenting agent comprises magnetizable rods.

9. A method for forming a sphincter surrounding a portion of a body lumen, the method comprising a step of injecting an active augmenting agent into tissue surrounding the lumen, wherein the active augmenting agent comprises magnetizable particles.

10. The method according to claim 9 wherein the magnetizable particles are suspended in a composition containing a carrier.

11. The method according to claim 10 wherein the magnetizable particles include a surface modifier.

12. The method according to claim 9 wherein the magnetizable particles are magnetically active when injected into the tissue.

13. The method according to claim 9 wherein the magnetizable particles are unmagnetized when injected into the tissue and subsequently magnetized after injection.

14. The method according to claim 9 wherein the magnetizable particles are about 30 to 3000 microns in size.

15. The method according to claim 14 wherein the magnetizable particles are about 80 to 600 microns in size.

16. A method of urging a patient's body tissue passageway toward closure comprising:
    implanting mutually attracting magnetic bodies in the patient's body at locations that are circumferential of the passageway.

17. The method defined in claim 16 wherein the locations include first and second locations that are adjacent respective opposite sides of the passageway.

18. The method defined in claim 16 further comprising:
    selecting the magnetic bodies so that their mutual magnetic attraction force is less than an opening force exerted on the passageway by a particular physiological occurrence.

19. The method defined in claim 16 where the implanting is performed so that at least two of the magnetic bodies can move toward and away from one another.

20. The method defined in claim 19 wherein the at least two magnetic bodies tend to move toward one another in response to mutual magnetic attraction.

21. The method defined in claim 20 wherein the at least two magnetic bodies can move away from one another in response to a physiological occurrence in the patient's body.

22. The method defined in claim 16 wherein the implanting of at least one of the magnetic bodies is at least in part in tissue of the passageway.

23. The method defined in claim 16 wherein the implanting of at least one of the magnetic bodies is at least in part radially outside a lumen of the passageway.

24. The method defined in claim 16 wherein the implanting comprises:
    introducing at least one of the magnetic bodies into the patient's body via tubular instrumentation.

25. The method defined in claim 16 wherein the implanting comprises:
   introducing tubular instrumentation into the patient's body;
   passing at least one of the magnetic bodies into the patient's body through the tubular instrumentation; and
   withdrawing the tubular instrumentation from the patient's body.

26. The method defined in claim 16 wherein the body tissue is an esophagus.

27. The method defined in claim 16 wherein the body tissue is a urethra.

28. The method defined in claim 16 wherein the body tissue is an anal sphincter.

29. A method of urging a patient's body tissue passageway toward closure comprising:
   implanting mutually attracting permanent magnetic bodies in the patient's body at locations that are spaced from one another circumferentially about the passageway.

30. A method of urging a patient's body tissue passageway toward closure comprising:
   implanting at least two mutually attracting permanent magnetic bodies in the patient's body at respective locations that are spaced from one another circumferentially about the passageway.

31. The method of claim 16 wherein:
   the implanting comprises placing first, second and third magnetic dipoles substantially within an annulus that has a circumference;
   the first and second dipoles being attracted to each other by a first force acting along the circumference;
   the second and third dipoles being attracted to each other by a second force acting along the circumference; and
   the first and second forces being of such magnitudes that the circumference increases to allow matter to pass through the passageway and decreases after the matter passes through the passageway.

32. The method of claim 31 further comprising estimating a first radial mechanical force, the radial force being applied by the annulus to tissue adjacent the passageway.

33. The method of claim 32 further comprising configuring the dipoles such that the annulus has a maximum radial mechanical force that is less than the first radial mechanical force.

34. The method of claim 32 further comprising configuring the dipoles such that the annulus has a maximum radial mechanical force that is substantially the same as the first radial mechanical force.

* * * * *